(12) United States Patent
Bruzzese

(10) Patent No.: US 8,829,048 B2
(45) Date of Patent: Sep. 9, 2014

(54) USE OF HIGHLY CONCENTRATED COMPOSITIONS OF SELECTED N-3 FATTY ACIDS FOR THE TREATMENT OF CENTRAL NERVOUS SYSTEM DISTURBANCES

(75) Inventor: Tiberio Bruzzese, Milan (IT)

(73) Assignee: Tiberio Bruzzese, Milan (IT)

( * ) Notice: Subject to any disclaimer, the term of this patent is extended or adjusted under 35 U.S.C. 154(b) by 1902 days.

(21) Appl. No.: 10/586,863

(22) PCT Filed: Jan. 20, 2005

(86) PCT No.: PCT/EP2005/000522
§ 371 (c)(1),
(2), (4) Date: Jul. 21, 2006

(87) PCT Pub. No.: WO2005/070411
PCT Pub. Date: Aug. 4, 2005

(65) Prior Publication Data
US 2007/0161705 A1 Jul. 12, 2007

(30) Foreign Application Priority Data
Jan. 21, 2004 (IT) .............................. MI2004A0069

(51) Int. Cl.
*A61K 31/202* (2006.01)
(52) U.S. Cl.
CPC .................................. *A61K 31/202* (2013.01)
USPC ......................................................... 514/560
(58) Field of Classification Search
CPC .................................................. A61K 31/202
USPC ......................................................... 514/560
See application file for complete search history.

(56) References Cited

U.S. PATENT DOCUMENTS

| | | | | |
|---|---|---|---|---|
| 4,753,964 | A | 6/1988 | Horrobin | |
| 4,977,187 | A * | 12/1990 | Horrobin | 514/560 |
| 5,120,760 | A | 6/1992 | Horrobin | |
| 5,130,061 | A | 7/1992 | Cornieri et al. | |
| 5,516,800 | A | 5/1996 | Horrobin | |
| 5,776,978 | A | 7/1998 | Bruzzese | |
| 6,306,907 | B1 * | 10/2001 | Nishikawa et al. | 514/558 |
| 6,331,568 | B1 | 12/2001 | Horrobin | |
| 6,384,077 | B1 * | 5/2002 | Peet et al. | 514/560 |
| 6,759,435 | B1 * | 7/2004 | Chen | 514/648 |

FOREIGN PATENT DOCUMENTS

| | | |
|---|---|---|
| DE | 3739700 | 6/1989 |
| EP | 0342795 | 11/1989 |
| EP | 0 347 056 | 12/1989 |
| EP | 0559576 | 9/1993 |
| EP | 0 599 576 | 6/1994 |
| EP | 0 699 437 | 3/1996 |
| EP | 1157692 | 11/2001 |
| GB | 2148713 | 6/1985 |
| GB | 2218904 | 11/1989 |
| GB | 2218984 | 11/1989 |
| IT | 1235879 | 11/1992 |
| WO | 8911521 | 11/1989 |
| WO | 0103696 | 1/2001 |
| WO | 02052955 | 7/2002 |

OTHER PUBLICATIONS

Mellor, Jan E. et al.,"Omega-3 Fatty Acid Supplementation in Schizophrenic Patients", Human Psychopharmacology, vol. 11, No. 1, pp. 39-46,1996.
Vreugdenhil, M et al.,"Polyunsaturated fatty acids modulate sodium and calcium currents in CA 1neurons", National Academy of Science. Washington, US. vol. 93, No. 22, pp. 12559-12563, Oct. 29, 1996.
Vreugdenhil, M et al.,"Anticonvulsant properties of polyunsaturated fatty acids", Society for Neuroscience, US, vol. 22, pp. 2106, 1996.
Voskuyl, Rob A., Is marine fat anti-epileptogenic?, Nutrition and Health 2002, vol. 16, No. 1, pp. 51-53, 2002.
Merck (Jun. 2008) "Schizophrenia", Merck Manual Home Edition.
"Announcement: Availability of fish oil test materials", The Journal of Nutrition—Official publication of the American Institute of Nutrition (1989) 119(10).
"Goodman & Gilman's the pharmacological basis of therapeutics", McGraw-Hill, Medical Publishing Division (2001) 10th ed.: 550; 560-561; 674-676; 669; 687; 1487 & 1534.
"Harrison's Principles of Internal medicine", McGraw-Hill (2001) 15th ed., Medical Publishing Division: 2548-2549.
"Omega-3-acid ethyl esters", European Pharmacopoeia Supplement (2000): 1008-1011.
"Omega-3-acid triglycerides", European Pharmacopoeia 9.0 Monograph (Jan. 2009): 2619-2621.
Appel et al., "Dietary fish oil (MaxEPA) enhances pancreatic carcinogenesis in azaserine-treated rats", British Journal of Cancer (1996) 73: 36-43.
Ballou et al., "Inhibition of human platelet phospholipase A2 activity by unsaturated fatty acids", Proc Natl Acad Sci USA (1985) 82: 371-375.
Burns et al., "Phase I clinical study of fish oil fatty acid capsules for patients with cancer cachexia: Cancer and leukemia group B—Study 9473", Clinical Cancer Research (Dec. 1999) 5: 3942-3947.
Deutsch et al., "Topiramate antagonizes MK-801 in an animal model of schizophrenia", Eur J of Pharmacology (2002) 449: 121-125.
Hashimoto et al., "Docosahexaenoic acid provides protection from impairment of learning ability in Alzheimer's disease model rates", J Neurochem (Jun. 2002) 81(5): 1084-1091.
Hsiao, "Correlative memory deficits, Aβ elevation, and amyloid plaques in transgenic mice", Science (1996) 274: 99-102.

(Continued)

*Primary Examiner* — Jennifer M Kim
(74) *Attorney, Agent, or Firm* — Novak Druce Connolly Bove + Quigg LLP

(57) ABSTRACT

The use is described of a composition comprising either a) alpha-linolenic acid (ALA, C18:3 n-3) or b) docosahexaenoic acid (DHA, C22:6 n-3) or c) DHA in admixture with eicosapentaenoic acid (EPA, C20:5 n-3), in a ratio of 1:0.5 to 1:1.7, respectively, and/or the pharmaceutically acceptable derivatives and/or precursors thereof; either a) or b) or c) being in a concentration not lower than 70% by weight of the total fatty acids weight in the composition, for the preparation of a drug for the prevention and/or treatment of the disturbances of the central nervous system (CNS) such as epilepsy, schizophrenia, bipolar (manic-depressive illness) and unipolar (major depression) psychiatric disorders, and by degenerative Alzheimer's disease and related forms of dementia.

8 Claims, No Drawings

(56) References Cited

OTHER PUBLICATIONS

Kosugi et al., "Synthesis of triacylglycerol from polyunsaturated fatty acid by immobilised lipase", JAOCS (1994) 71(12): 1397.

Lim et al., "Ibuprofen suppresses plaque pathology and inflammation in a mouse model for Alzheimer's disease", J of Neuroscience (2000) 20(15): 5709-5714.

Porsolt et al., "Rodent models of depression: Forced swimming and tail suspension behavioral despair tests in rats and mice", Curr Protoc Neuroscience (May 2001) Chapter 8, Unit 10.A.

Rambjor et al., "Eicosapentaenoic acid is primarily responsible for hypotriglyceridemic effect of fish oil in humans", Lipid (1996) 31 Supplement: S45-S49.

Simonpoulos, "Evolutionary aspects of diet, the omega-6/omega-3 ratio and genetic variations: Nutritional implications for chronic diseases", Biomedicine and Pharmacotherapy (2006) 60: 502-507.

Standaert et al., "Treatment of central nervous system degenerative disorders", McGraw-Hill, Medical Publishing Division (2001) 10th ed.: 549.

Stoll et al., "Omega 3 fatty acids in bipolar disorder—A preliminary double-blind, placebo controlled trial", Arch Gen Psychiatry (1999) 56: 407-412.

Su et al., "Omega-3 fatty acids in major depressive disorder. A preliminary double-blind, placebo-controlled trial", Eur Neuropsychopharmacol (Aug. 2003 13(4): 267-271.

Woodman et al., "Effects of purified eicosapentanoic acid and docosahexaenoic acids on glycaemic control, blood pressure, and serum lipids in type 2 diabetic patients with treated hypertension", American Journal of Clinical Nutrition (2002) 76: 1007-1015.

Yamada et al., "Protective effects of idebenone and α-tocopherol on β-amyloid-(1-42)-induced learning and memory deficits in rats: Implication of oxidative stress in β-amyloid-induced neurotoxicity in vivo", Eur J of Neuroscience (1999) 11:83-90.

Yu et al., "Total syntheses and anticholinesterase activities of (3a$S$)-$N$(8)-Norphysostigmine, (3a$S$)-$N$(8)-Norphenserine, their antipodal isomers, and other $N$(8)-substituted analogues", J Med Chem (1997) 40: 2895-2901.

\* cited by examiner

USE OF HIGHLY CONCENTRATED COMPOSITIONS OF SELECTED N-3 FATTY ACIDS FOR THE TREATMENT OF CENTRAL NERVOUS SYSTEM DISTURBANCES

The invention refers to the use of highly concentrated compositions of selected n-3 fatty acids for the treatment of central nervous system disturbances. In particular, the invention concerns the use of a composition comprising either alpha-linolenic acid (ALA, C18:3 n-3) or docosahexaenoic acid (DHA, C22:6 n-3) or DHA in admixture with eicosapentaenoic acid (EPA, C20:5 n-3) and/or the pharmaceutically acceptable derivatives and/or precursors thereof, in a high concentration, for the preparation of a drug for the prevention and/or treatment of the disturbances of the central nervous system (CNS), both of psychiatric relevance and of neurological type.

The expression "central nervous system disturbances" is commonly meant to indicate the cluster of convulsive symptoms usually included in the so-called epileptic syndromes, as well as to the most severe psychiatric disorders, represented by the various schizophrenia forms, by the manic-depressive syndromes, by the severe depression, and by the Alzheimer's disease and the related forms of dementia.

The term epilepsy refers to disorders of brain function characterized by periodic and unpredictable occurrence of seizures. Such seizures are constituted by transient alterations of behaviour caused by disordered, synchronous and rhythmic firing of neuronal brain populations, not induced by evident provocation.

These seizures are thought to arise from disorders of cerebral cortex, not involving other CNS structures, and their behavioural manifestations is determined by the functions served by the involved cortical site. For instance, a seizure arising from the motor cortex will induce f.i. clonic jerking of the body muscles controlled by this same region of the cortex. Epileptic seizures are defined partial, when beginning focally in a cortical site, or generalized seizures, when involving both hemispheres. A partial seizure is defined simple, if associated with preservation of consciousness, or complex in the opposite case, often due to impairment of the temporal lobe. A typical generalized epileptic seizure includes absence and tonic-clonic convulsions.

Schizophrenia is caused by a chemical imbalance in the brain induced, in its turn, by triggering causes of genetic or environmental origin (autoimmune diseases, infections during development, psychological trauma, etc.), involving—among other effects—overproduction of dopamine. There are several categories of the disease: paranoid, catatonic, disorganised, undifferentiated schizophrenia.

Patients start to get a great variety of symptoms, which anyway can reveal themselves into two typical forms: negative symptoms, such as withdrawal, apathy, depression, blunted emotions, and positive symptoms, such as hallucinations, misunderstanding of reality and of perception, disordered thinking and speech. The appearance of the disease is early, but diagnosis is complex and can take very long times.

The older drugs, typical neuroleptic drugs, essentially agents blocking cerebral dopamine, are however poorly selective and associated with heavy side effects on dopamine-related functions, including severe extrapyramidal effects, like unusual and involuntary body movements (dyskinesias, tardive dyskinesias), restlessness (alkathesia), muscle spams (dystonia), as well as impairment of cognition, reduced libido, etc; further, these drugs while moderately effective in treating positive symptoms, are quite unsuccessful on negative symptoms, as depression and apathy.

The more recent drugs, so-called atypical drugs, have a broader action spectrum and less side effects, such as the arising of involuntary movements, but are unavailable in under-developed countries because of their expensiveness, and are not free anyway from other effects, even highly risly (prolongation of QTC interval of ECG, weight gain, diabetic symptoms).

The syndromes of bipolar disturbances (manic-depressive disorders) and of severe unipolar depression (major depression) constitute the more severe disorders of mood or affect. They usually include disordered autonomic functioning (i.e., altered activity rhythms, sleep and appetite) and behaviour, as well as persistent abnormalities of mood and increased risk of self-destruction or suicide.

Alzheimer's disease, as other degenerative disease of CNS, all induced by progressive loss of neurons from specific regions of the brain, is characterized by marked atrophy of the cerebral cortex and loss of cortical, sub-cortical and hippocampal neurons; a parallel reduction of neurotransmitters has also been evidenced, in particular of acetylcholine, which has given rise to the cholinergic hypothesis of the disease and led to the few drugs of some limited effectiveness.

The disease produces a progressive impairment of the cognitive abilities, which is typical—but not exclusive—of the elder subject. The disease appears first as an impairment of short-term memory, but as the condition progresses additional cognitive abilities are impaired, such as the ability to calculate, exercise visual-spatial skills, and use common objects (ideo-motor apraxia), and the illness reveals itself in various forms of dementia. Later on, death often comes up from a complication of immobility, such as pneumonia.

For all mentioned pathologies, there are not valid pharmacological and clinical treatments, able to modify the progression of the disease. In all cases only symptomatic treatments are adopted, only able to alleviate the symptomatology and, if endowed with some efficacy, only effective on a very limited number of patients: for instance the standard treatments in the depression permit to obtain until a maximum of 50% reduction of score in the evaluation scale in two thirds of patients, while improvements in schizophrenia are obtained in the order of 20-30%, and treatments in the Alzheimer's disease result to be only ineffective palliatives.

Some therapeutic effects of the n-3 polyunsaturated fatty acids are already well known. For instance, IT 1,235,879, U.S. Pat. Nos. 5,502,077 and 5,656,667 disclose their effect on multiple risk factors for cardiovascular illnesses, as hypertriglyceridemia, hypercholesterolemia and hypertension.

EP-A-0409903 describes the preparation of high concentration mixtures of EPA and DHA or their esters, useful in the treatment of hyperlipemia, thrombosis, myocardial infarct, platelet hyperaggregation and related vascular pathologies, as well as of acute and chronic inflammations, autoimmune syndromes, and in the tumour prevention. DHA, which is contained in high concentration in the retina, is also active on the functionality of sight, on ceroidosis and on learning and ageing processes.

WO 00/48592 discloses the use of mixtures of EPA and DHA ethyl esters for the secondary prevention of "sudden death" in patients who have already suffered a myocardial infarct. It also results in the scientific literature that the n-3 polyunsaturated acids, particularly DHA, are contained in high concentration in the cerebral cortex (much less in the white matter), according to O'Brien J S and Sampson E L, J. Lipid Res. 6, 545, 1965, in the retina (Anderson R E, Exp. Eye Res. 10, 339, 1970), in the testis and sperm (Poulos A et al., Comp. Biochem. Physiol. 46B, 541, 1975) of all mammals, including human beings.

DHA is therefore one of the most abundant components of the brain's structural lipids, in which its presence can derive only from direct ingestion or by synthesis from the dietary precursor, i.e. alpha-linolenic acid (ALA).

Among others, Neuringer M et al., J. Clin. Invest. 73, 272, 1984; Proc. Natl. Acad. Sci. USA 83, 4021, 1986, suggest that n-3 fatty acids are essential for a normal prenatal and postnatal development of retina and brain.

EP-A-0347056 discloses the use of gamma-linolenic acid (GLA, C18:3 n-6) and higher n-6 acids, and of stearidonic acid (SA, C18:4 n-3) and higher n-3 acids, for the preparation of a drug for treatment of tardive dyskinesias.

EP-A-0599576 describes the use of a combination of arachidonic acid (AA, C20:4 n-6) and DHA, acids belonging to the n-6 and n-3 series respectively, to obtain a drug effective on the negative syndrome of schizophrenia, in subjects with low levels of the two acids in the cell membranes.

U.S. Pat. No. 6,331,568 discloses a method for treating schizophrenia by administration of EPA or SA, two n-3 acids, and optionally of n-6 acids. The compositions therein disclosed show a ratio of EPA or SA to DHA of not less than 3:1, 4:1, or more.

WO 00/44361 discloses a pharmaceutical preparation containing at least 90% or more of EPA, and less than 5% of DHA for uses similar to the ones of the documents just above discussed.

U.S. Pat. No. 5,120,763 and EP 0366480 disclose a composition containing 13.0-27.5% of linolenic acid (i.e. ALA, C18:3 n-3) and 87.0-72.5% of linoleic acid (i.e. LA, C18:2 n-6), useful in the treatment of Alzheimer's disease and related syndromes, while U.S. Pat. No. 5,468,776 describes the same components in the more limited range of 16.7-22.2% and 83.3-77.8% respectively.

Although it is known to a certain degree that compositions comprising peculiar combinations of n-3 and/or n-6 fatty acids may have shown some effectiveness on pathologies such as schizophrenia or Alzheimer's disease, a clear indication on their activity against such pathologies cannot yet be taken from the prior art since the discussion in the scientific community is quite controversial and still open.

For instance, while Mellor et al., Human Psychopharmacology, 11, 39-46, 1996 disclosed the effectiveness of some n-3 acids, such as DHA, carrying out their experiments using a composition comprising EPA 18% and DHA 12%, in U.S. Pat. No. 6,331,568 there is pointed out that such ability has to be denied on the basis of both clinical control and for biochemical reasons.

It has been now surprisingly found that some other peculiar compositions comprising n-3 fatty acids in very high concentrations are effective for the prevention and/or treatment of various and severe disorders of the central nervous system, both of neurological type and of psychiatric pertinence, as for instance epilepsy and as schizophrenia, the manic-depressive disturbances and the major depression, as well as the degenerative neuronal disorders typical of Alzheimer's disease.

According to a first aspect the invention refers to the use of a composition comprising either
  a) alpha-linolenic acid (ALA, C18:3 n-3) and/or the pharmaceutically acceptable derivatives and/or precursors thereof; or
  b) docosahexaenoic acid (DHA, C22:6 n-3) and/or the pharmaceutically acceptable derivatives and/or precursors thereof; or
  c) DHA in admixture with eicosapentaenoic acid (EPA, C20:5 n-3), in a ratio of 1:0.5 to 1:1.7, preferably of 1:0.9 to 1:1.5, respectively, and/or the pharmaceutically acceptable derivatives and/or precursors thereof;

either a) or b) or c) being in a concentration not lower than 70% by weight of the total fatty acids weight in the composition, for the preparation of a drug for the prevention and/or treatment of the disturbances of the central nervous system (CNS), both of psychiatric relevance and of neurological type.

Preferably, the concentration in either a) or b) or c) is of 75% to 95%, in particular of 80% to 90%, most preferably of 85% (as a mean value).

Among the disturbances of CNS which can be prevented and/or treated according to the invention, there are epilepsy (showing partial and/or generalized seizures or simple and/or complex seizures), schizophrenia (showing negative and/or positive symptoms and being either paranoid or catatonic or disorganised or undifferentiated schizophrenia), manic-depressive syndrome, major depression (including disorders of mood, behaviour and autonomic functions correlated to activity, sleep and appetite), and Alzheimer's disease (including the various related forms of dementia).

In a preferred embodiment, the drug suitable for the use of the invention comprises essentially DHA ethyl ester and EPA ethyl ester.

Yet, according to another preferred embodiment, the composition can also comprise at least another n-3 and/or n-6 polyunsaturated and/or monounsaturated and/or saturated fatty acid, in particular the composition can comprise at least two other n-3 and/or n-6 polyunsaturated and/or monounsaturated and/or saturated fatty acids, in any ratio among themselves; the other n-3 and/or n-6 polyunsaturated and/or monounsaturated and/or saturated fatty acids are in a concentration of lower or equal to 30%.

Preferred ALA, DHA, and EPA derivative are selected among $C_1$-$C_3$ alkyl esters (preferably ethyl esters), glyceride mono-, di-, tri-esters, and salts with pharmaceutically acceptable bases, like for instance sodium hydroxide and potassium hydroxide, aminoalcohols as ethanolamine and choline, basic aminoacids as arginine and lysine. "Precursor" is herein meant to indicate any compound able to lead to ALA, DHA and EPA through in vivo transformations, f.i. through metabolic processes.

Also the compositions reported in the European Pharmacopoeia 2000, Eu. Ph. 2000, having a content of not less than 80% of the mixture of the ethyl esters of EPA and DHA (not less than 40% and 34%, respectively) and not less than 90% total ethyl esters of n-3 polyunsaturated fatty acids, will be suitable for the use of the present invention.

All the above mentioned compositions, as well as the pharmaceutical preparations which can be derived therefrom, can be prepared according to methods known to the expert in the field, as f. i. those described in U.S. Pat. No. 5,130,061, WO 89/11 521, IT 1 235 879, DE 3 739 700, JP 02/25 447 (and others), herein incorporated by reference as far as their preparation is concerned.

Commonly, the composition suitable for the use of the invention can be obtained by extraction, concentration and purification processes starting from natural sources, typically from fish oils or other marine source as algae (for DHA and EPA), or even from vegetable oils, f.i. seed oils (typically for ALA), as well as by means of semi-synthetic transformation processes, when required.

Together with their efficacy to the aim of the pharmaceutical and therapeutic use of the invention, the above compositions show a very high clinical tolerance, almost free from any side-effect, with exclusion of some uncommon effect on the intestinal peristalsis, and can be obtained with low production costs from natural sources, which strongly helps their diffusion in low economic potential countries, differently from the poor availability of some totally synthetic drugs.

The drug suitable for the use of the invention is preferably administered by oral route, particularly in the form of soft jelly capsules; yet, the other typical administration routes, usual in the pharmaceutical technology, are not excluded. The dose per unit includes usually 100-1000 mg of the above specified n-3 polyunsaturated fatty acids and/or derivatives and/or precursors, preferably 300-1000 mg or better 500 mg or more often 1000 mg. The mean total dose is 0.1-5 g per day, even in intermittent administration, according to the need and advice of the physician, preferably 0.3-3 g per day or particularly 1-2 g. An effective dose meanly corresponds to 2-60 mg/kg/day.

Obviously, the drug suitable for the use of the invention can be administered also under other forms appropriate for the oral administration such as, for instance, hard oil-proof capsules or tablets wherein the fatty acids are pre-adsorbed on solid matrices.

It is also possible to use oily emulsions, syrups, drops, granulates in dispersing excipients, etc., as well as other forms able to guarantee a systemic absorption by means of other administration routes, f. i. sterile emulsions or solutions suitable for parenteral injective use, as it will be apparent to the man skilled in the art.

The drug suitable for the use of the present invention can be used alone, as a mono-therapy, or as a drug coadjuvant or auxiliary to at least another active principle or drug effective for the prevention and/or treatment of the disturbances of CNS, or can even be used in direct combination, including said at least another active principle or drug endowed with an activity similar or complementary or synergic to that one of the above defined drug suitable for the use of the invention.

Typical examples of such at least another active principle or drug to which the drug suitable for the use of the invention can be combined or can be auxiliary or coadjuvant by co-administration, are, without any limitative meaning:

in the treatment of epilepsy, carbamazepine, phenytoin, phenobarbital, primidone, valproate, gabapentin, lamotrigine, clonazepam, ethosuximide, and related structures;

in the treatment of schizophrenia, drugs of the group of phenothiazines, thioxanthenes, dibenzoazepines, butyrophenones, indolones, phenyl- and diphenylpiperidines, etc., among them the typical neuroleptic agents as chlorpromazine, thioridazine, haloperidol, sulpiride, and pimozide, and others, and the antipsychotic "atypical" agents as clozapine, quetiapine, olanzapine, sertindole, risperidone, ziprasidone, amisulpiride and others;

in the treatment of major depression and of manic-depressive illness, the antidepressant drugs of the group of tricyclic norepinephrine reuptake inhibitors as amitriptyline and others, of the group of serotonin reuptake inhibitors as fluoxetine, paroxetine, sertraline and others, of the group of monoamine oxidase (MAO) inhibitors as phenelzine and others, of the group of "atypical" drugs as bupropion and trazodone; the antimanic drugs as lithium salts; the drugs acting on mood and affect disorders as many antianxiety agents, including benzodiazepines and the above mentioned antidepressant and antimanic drugs as well as some anticonvulsants/anti-epileptic drugs as carbamazepine and valproate;

in the treatment of Alzheimer's disease, among the few "approach" drugs, the precursors of acetylcholine, as choline and phosphatidylcholine, and the inhibitors of catabolic enzyme (acetylcholinesterase, AChE), as physostigmine, tacrine, donepezilrivastigmine and galantamine, as well as memantine, more recently adopted and endowed with a different mechanism of action.

The composition suitable for the use of the invention can also comprise a pharmaceutically acceptable diluent, and/or a vehicle, and/or a binder, and/or thickener, and/or a surfactant, as well as a lubricant, aromatizer, colorant, sweetener, stabilizer and the like, as it will be apparent to the man skilled in the art. Among the stabilizer agents, antioxidants, particularly tocopherol (vitamin E) and the like, as well as ascorbyl palmitate, hydroxytoluene, butylhydroxyanisole and the like known in the art, are particularly preferred.

As already illustrated above, the drug comprising either a) or b) or c) as above defined can be administered according to the invention either as a single drug or in fixed pharmaceutical combination with other known drugs already known to be used in the same pathologies, or even as substances coadjuvant to said known drugs, under separated administration.

According to another aspect, the invention relates to a method for prevention and/or treatment of CNS disturbances, as above illustrated, in a mammal in need thereof comprising administering to the mammal a therapeutically effective dose, preferably ranging from about 2 to 60 mg/kg of the mammal body weight per day, of a drug as above described.

The following examples illustrate the invention without limiting it.

EXAMPLE 1

A few compositions of the invention are illustrated in the following Table and can be prepared according to the methods described in U.S. Pat. No. 5,130,061 (compositions A, C, D, E), IT 1235879 (composition B), WO 89/11521 (compositions F, H, I) and DE 3739700 (composition G), and are anyway easily available even using other preparative methods (JP 02/25447 and several others).

The quantities indicated in the Table express percentages by weight on the total weight of fatty acids. Other n-3 acids, as well as n-6 unsaturated acids, having different length and/or unsaturation degree, monounsaturated and saturated, can be present in limited quantities. Antioxidant: alpha-tocopherol (mean<0.3%; even much higher concentrations can be used).

|   | A 1) | B 1) | C 1) | D 1) | E 1) | F 1) | G 1) | H 2) | I 3) |
|---|---|---|---|---|---|---|---|---|---|
| EPA | >40 | >44 | >40 | >35 | >30 | <15 |   | >40 | >50 |
| DHA | >34 | >30 | >34 | >30 | >35 | >80 |   | >30 | >30 |
| EPA + DHA | >85 | >80 | >80 | >70 | >70 | >85 |   | >80 | >80 |
| Esters 4) |   | >3 |   |   |   |   |   |   |   |
| Total n-3 esters 5) |   |   | >90 |   |   |   |   |   |   |
| ALA |   |   |   |   |   |   | >70 |   |   |

1) ethyl esters;
2) free acids;
3) sodium salts;
4) ethyl esters of other (C20, C21, C22) n-3 acids;
5) total ethyl esters of n-3 acids.

EXAMPLE 2

The compositions of the following Table, relative to soft gelatin capsules containing 1 g ethyl esters of polyunsaturated fatty acid, were prepared by methods known in the art.

|                  | A (mg)   | B (mg)      | C (mg)   |
|------------------|----------|-------------|----------|
| EPA 1)           | 525      |             | >400     |
| DHA 1)           | 315      |             | >340     |
| EPA + DHA 1)     |          | 850         | >800     |
| Total n-3 1)     |          |             | >900     |
| d-tocopherol     | 4 Units  |             | 4 Units  |
| d,l-tocopherol   |          | 0.3         |          |
| Gelatine         | 246      |             | 246      |
| Gelatine succinate |        | 233         |          |
| Glycerol         | 118      | 67          | 118      |
| RIO              | 2.27     |             | 2.27     |
| YIO              | 1.27     |             | 1.27     |
| SHB + SPHB       |          | 1.09 + 0.54 |          |

1) ethyl esters;
RIO: red iron oxide;
YIO: yellow iron oxide;
SHB: sodium p.hydroxybenzoate;
SPHB: sodium propyl p.hydroxybenzoate.

EXAMPLES 3-6

Pharmacological Activity

The effectiveness of the composition suitable for the use of the invention in the prevention and/or treatment of CNS disturbances as those above described, as well as of the possibility of their pharmaceutical and clinical use, has been demonstrated following several pharmacological tests which permitted a wide testing on small size animals (mice, rats), without the ethical implications proper of testing in humans.

A first model of experiment evaluated the protection against epileptic seizures induced by direct application of iron chloride to cerebral cortex; a second model examined the protective effect against a known convulsant chemical agent (pentylenetetrazol); a third model verified the effect on the induction of epileptic seizures provoked by repeated subconvulsive dose administration of the same chemical agent and a fourth experimental model evaluated the effect protective on the anomalous behaviour induced, in the form of irregular jumping, by the administration of dizocilpine, an analogue of phencyclidine which binds similarly to N-methyl-D-aspartate (NMDA) receptors provoking its hypofunction and inducing schizophreniform psychosis.

In some of such tests, attention has been particularly addressed to detect any activity strengthening or coadjuvant to that of other known drugs.

Male Sprague-Dawley albino rats, about two months of age and 200-240-g weight, were used in the experiments of Examples 3-5. The animals were housed at an average temperature of about 22° C. and an average relative humidity of 40-50%, with artificial daily light cycles of 12 hours. In example 6, male Swiss mice weighing 22-30 g, housed in similar room conditions, were used.

EXAMPLE 3

Two groups of 15 rats were treated for 2 weeks by intraperitoneal (i.p.) route with 50 mg/kg of composition B (Example 1) containing >80% EPA and DHA ethyl esters (group 1) and with saline solution (group 2, control), respectively. At the end, all rats received a dose of 5 microlitres of 100 mM solution of $FeCl_3$, directly injected through unilateral left-side cannula into the anterior amygdala area. The administration of $FeCl_3$ into the cerebral cortex or amygdala-hippocampus complex is able to induce an epileptic focus, according to Willmore L. J., Science, 200, 1501, 1978. By prolonged direct monitoring, the number of animals protected or subject to major motor epileptic seizures are determined, as evidenced by tonic- clonic contractions of the limbs, trunk and head, lack of straightening reflex, saliva and blood discharge from the mouth.

Results: animals responding with seizures:
3/15 (group 1, treated)
14/15 (group 2, control)

EXAMPLE 4

In a preliminary experiment, the dose effective on 50% of study strain rats of a known epileptogenic agent (pentylenetetrazol) injected by intraperitoneal route, has been determined, obtaining an ED50 value of approximately 70-75 mg/kg i.p.

Four groups of 10 rats each were treated daily for 2 weeks, by i.p. route, with 50 mg/kg of a composition of n-3 fatty acids having >85% of EPA and DHA ethyl esters according to Example 1, composition A (group 1), with 5 mg/kg of a known antiepileptic drug represented by clonazepam (group 2), with the same doses in combination (group 3) and with saline solution (group 4, control). At the end, all the groups were treated with 100 mg/kg i.p. of pentylenetetrazol, and the animals underwent the following control exams: 1) length of latency period to the first major motor seizures (tonic- clonic contractions of the limbs, trunk and head; falling; saliva and blood discharge from the mouth); 2) number of rats responding with major motor seizures (or protected from seizure); 3) mean duration of the major motor seizure (MMS); 4) number of rats presenting minor clonic contractions (MCC), such as a sudden flexion of the forelegs or extension of the rear legs; 5) number of rats who died within 20 minutes or 5 hours after pentylenetetrazol injection.

The obtained results (mean±standard deviation) are reported in the following Table:

| Treatment groups | Latency to seizures (sec.) | Duration of seizures (sec) | Rats with MMS (n/tot) | Rats with MCC (n/tot) | Dead animals <20' | Dead animals <5 h |
|---|---|---|---|---|---|---|
| 1) (n-3) | 184 ± 23 | 22 ± 9 | 1/10 | 2/10 | 1/10 | 3/10 |
| 2) (clonazepam) | 203 ± 12 | 25 ± 6 | 1/10 | 3/10 | 2/10 | 4/10 |
| 3) (n-3 + clonazepam) | 265 ± 15 | 15 ± 7 | 0/10 | 1/10 | 0/10 | 2/10 |
| 4) (control) | 12 ± 4 | 786 ± 34 | 9/10 | 1/10 | 10/10 | 0/10 |

It appears from such data that the pre-treatment with the composition of EPA and DHA ethyl esters is able to significantly protect the rats (about 90%) from major motor seizures induced by the administration of pentylenetetrazol. In the few animals not protected, the seizure is anyway delayed in the time and its duration is noticeably lower. Also a strong reduction of mortality during the convulsive period is noticed, with partial protection even during the post-ictal period. The effectivenss of the composition is at least similar to that of a reference drug and is noticeably potentiated if administered in combination.

EXAMPLE 5

Two groups of 10 rats each were daily treated for 2 weeks, by i.p. route, with 50 mg/kg of a composition >80% of EPA and DHA ethyl esters, according to Example 1, composition C (group 1), and with saline solution (group 2, control). At the end all the animals were administered at 15 min. intervals a series of sub-convulsive doses of pentylenetetrazol (15 mg/kg, i.p.), so determining the number of injections required to produce an attack of clonic or tonic-clonic convulsions of forelegs and hind legs, followed by loss of straightening reflex.

Results: number of sub-convulsive doses for induction of seizure (mean±standard deviation):
16.35±3.20 (group 1, treated)
3.26±1.54 (group 2, control).

EXAMPLE 6

Two groups of 12 mice each were treated daily for 2 weeks, by i.p. route, with 50 mg/kg of a composition >80% of EPA and DHA ethyl esters according to Example 1, composition B (group 1), and with saline solution (group 2). At the end all the animals received by i.p. route 1 mg/kg of dizocilpine, an analogue of phencyclidine able to bind the N-methyl-D-aspartate (NMDA) receptors, inducing its hypofunction and subsequent schizophreniform psychosis. The behaviour induced in the mouse consists in eliciting irregular and intense jumping (so-called popping), and its attenuation represents a valid experimental model to identify substances able to counteract the pathophysiology of schizophrenia (Deutsch S.I. et al., Neuropsychopharmacology, 15, 37, 1996; ibidem, 15, 329, 1996). The administration of dizocilpine was followed by monitoring for 30 minutes, and during the period the popping behaviour, i.e. the number of jumping of treated and control animals was registered by a suitable equipment.

Results: number of induced jumps:
45±12 (group 1, treated)
338±55 (group 2, positive control).

The invention claimed is:

1. A method for the treatment of schizophrenia comprising administering to a subject in need thereof a composition consisting essentially of, in a concentration expressed as % by weight of the total fatty acid weight in the composition, DHA ethyl ester >34 and EPA ethyl ester >40, wherein EPA+DHA ethyl esters >80, the total ethyl esters of n-3 acids being >90.

2. The method according to claim 1, wherein the composition is administered by oral route.

3. The method according to claim 1, wherein the composition is in the form of soft gelatine capsules.

4. The method according to claim 1, wherein the composition is administered at the dose of 0.1-5 g/day.

5. The method according to claim 1, wherein the composition is administered at the dose of 0.3-3 g/day.

6. The method according to claim 1, wherein the composition is administered at the dose of 1-2 g/day.

7. The method according to claim 1, wherein the composition is administered separately, as a coadjuvant or an auxiliary drug, from at least another drug effective for the treatment of schizophrenia.

8. A method for the treatment of schizophrenia comprising administering to a subject in need thereof a composition consisting essentially of, in a concentration expressed as % by weight of the total fatty acid weight in the composition, DHA ethyl ester >34 and EPA ethyl ester >40, wherein EPA+DHA ethyl esters >80, the total ethyl esters of n-3 acids being >90; and at least another drug effective for the treatment of schizophrenia.

* * * * *